United States Patent [19]
Green

[11] 4,061,914
[45] * Dec. 6, 1977

[54] METHOD AND APPARATUS FOR DUAL RESOLUTION ANALYSIS OF A SCENE

[76] Inventor: James Edmond Green, P.O. Box 734, Fayetteville, Tenn. 37334

[*] Notice: The portion of the term of this patent subsequent to July 20, 1993, has been disclaimed.

[21] Appl. No.: 682,970

[22] Filed: May 4, 1976

Related U.S. Application Data

[63] Continuation-in-part of Ser. No. 526,896, Nov. 25, 1974, Pat. No. 3,970,841.

[51] Int. Cl.² .................. H01J 39/12; G01N 33/16
[52] U.S. Cl. ................................. 250/201; 250/208; 250/222 PC; 250/578; 356/39
[58] Field of Search ............. 250/201, 203, 208, 209, 250/222 PC, 548, 578; 356/39, 40; 350/37, 40; 235/92 PC

[56] References Cited

U.S. PATENT DOCUMENTS

| | | | |
|---|---|---|---|
| 3,448,271 | 6/1969 | Aldrich et al. | 250/203 |
| 3,614,449 | 10/1971 | Ward | 250/203 |
| 3,804,976 | 4/1974 | Gard | 250/203 X |
| 3,864,564 | 2/1975 | Adkins | 250/201 |
| 3,970,841 | 7/1976 | Green | 250/201 |

*Primary Examiner*—Eugene R. La Roche
*Attorney, Agent, or Firm*—Richard J. Birch

[57] ABSTRACT

A method and apparatus for analyzing a scene at a low resolution until an object of interest is detected. Thereafter, the object of interest is analyzed at a higher resolution while continuing to analyze the scene at the low resolution. In the preferred embodiment, the scene comprises a blood sample and the objects of interest are blood cells.

18 Claims, 8 Drawing Figures

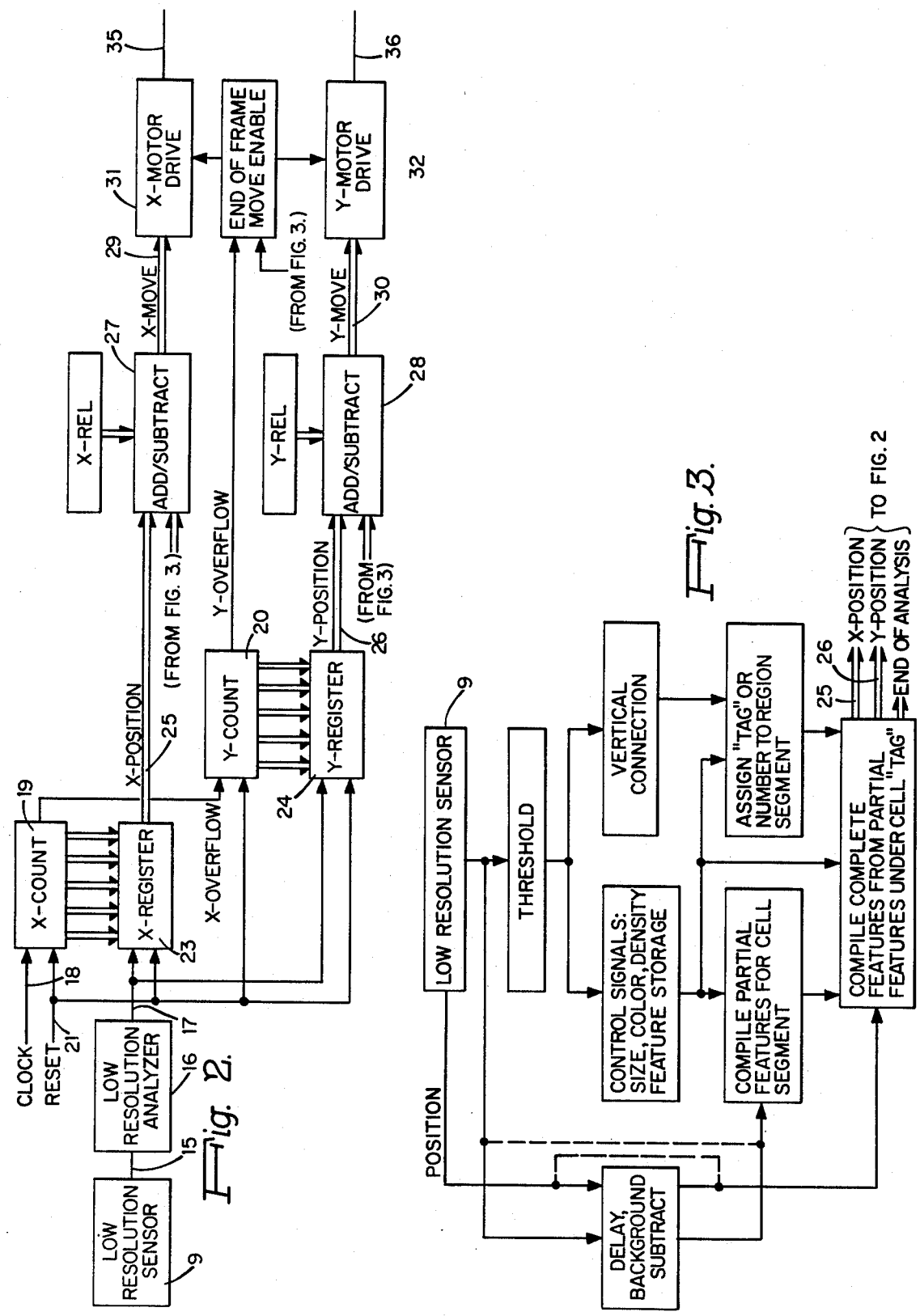

METHOD AND APPARATUS FOR DUAL RESOLUTION ANALYSIS OF A SCENE

CROSS-REFERENCE TO RELATED APPLICATIONS

This application is a Continuation-In-Part Application of Application Ser. No. 526,896, filed Nov. 25, 1974, now U.S. Pat. No. 3,970,841, by James E. Green for METHOD AND APPARATUS FOR DUAL RESOLUTION ANALYSIS OF A SCENE, which in turn was copending with Application Ser. No. 286,043, now U.S. Pat. No. 3,851,156, issued Nov. 26, 1974 to James E. Green.

BACKGROUND OF THE INVENTION

The present invention relates to scene analysis apparatus and methods and more particularly, to a method and apparatus for analyzing a scene at two different resolutions.

In many areas of particle analysis, such as, blood cell analysis or pap smear analysis, the particles of interest are widely distributed in a field and are surrounded by many particles of no interest at all. For example, white blood cells may be surrounded by hundreds of red blood cells while cancerous or dysplastic cervical cells may be surrounded by tens-to-thousands of normal cervical cells and debris.

It is desirable to analyze in detail only the particles of interest in the scene. This can be accomplished by the detailed analysis of all objects in order to exclude the unwanted objects. However, this technique is very time-consuming and therefore relatively impractical from a commercial standpoint. Alternately, one can use a single sensor to perform a preliminary analysis of all particles at a low resolution and then switch the sensor to a higher resolution for further analysis when a particle of interest is found in the sample. However, this method requires mechanical or electrical switching of the analysis resolution with a concomitant limitation of a single mode of analysis at any given time.

The use of simultaneous multiple resolution analysis of a plurality of fields overcomes the limitations of prior art analysis systems. Dual resolution scanning systems have been used by several workers. Aldrich et al disclose in U.S. Pat. No. 3,448,271 a dual resolution scanning system which centers and tracks celestial objects. In this system two coaxial images at different magnifications are employed to acquire and track stars or the solar disc. The scanned output of a single sensor is used as an on or off-axis signal in a feedback loop to center the star image on the optical axis. No image analysis of the celestial objects is performed or envisioned. In fact, the superimposed images on the single detector would confuse an attempt to analyze the scanner output.

Simularly, Ward in U.S. Pat. No. 3,614,449 discloses a dual resolution scanning system for acquiring and tracking a distant source of light (the target). Ward describes the same type coaxial dual resolution system in which both images are projected onto a single sensor. In addition, there is a second sensor responsive to a narrow spectral band ranging source emitted by the systen and reflected by the target. Although the ranging subsystem is functionally separate from the dual resolution centering and tracking system, it is housed in the same assembly for compactness in a NASA application. Again, there is no inmage analysis disclosed or envisioned by either the acquiring-tracking system or the ranging subsystem.

Other uses of dual resolution scanning have been disclosed, such as Gard in U.S. Pat. No. 3,804,976, which uses the scanned images for display purposes. However, no image analysis is revealed or envisioned by these disclosures.

Adkins in U.S. Pat. No. 3,864,564 discloses a dual resolution scanning system in which a low resolution, one dimensional scan is used for finding and positioning a blood cell, and a high resolution two-dimensional scan is used to analyze the cell. The high resolution sensor is a videcon type T.V. camera which is well suited to the analysis of the centered blood cell. However, the low resolution sensor is a single photodetector. The image is swept across the photodetector by means of a rotating mirror thereby producing a one-dimensional line scan of the low resolution scene. The low resolution signal is used only to detect and center the cell for analysis by the high resolution sensor. Analysis by the low resolution portion of the system is not disclosed or envisioned. In fact, any analysis using the onedimensional information provided by the low resolution line scanner would be difficult and limited.

A system such as that described by Adkins has several limitations. To use the blood cell example, if there were several classses of cells detected by the low resolution acquisition and centering system, and it was desired to perform a detailed analysis on only a subset of these cells, it would be necessary to acquire and center all detected cells and perform a detailed analysis on them all using Adkins system. Thus much additional unnecessary effort would be necessary. In the case of pap smears, where there may be thousands of normal cells to every cancer cell, the extra work necessary to perform a detailed analysis on every normal cell to find a single cancer cell would render a commercial application impractical.

In many cases it is possible to derive enough information from a preliminary low resolution analysis to determine if a detected object warrants further detailed analysis. The present invention provides for such dual resolution analysis with the low resolution analysis of a large field occurring simultaneously with the high resolution analysis of an object of interest. Using the previously mentioned blood cell example, artifacts such as dirt or large stain crystals can and do occur on blood smears. A simple preliminary measurement of object size is usually adequate to allow exclusion of these artifacts from the detailed high resolution analysis. A more complex low resolution analysis can be employed if desired It is accordingly, a general object of the invention to provide a method and apparatus for scene analysis which overcomes the limitations of the prior art systems.

It is a specific object of the invention to provide a method and apparatus for dual resolution analysis of a scene.

In the accomplishment of these objects, two sensors are employed: one covering a large field at a low resolution and the other covering a smaller field at a higher resolution. The low resolution field of view (large field) is located in a known relationship to the higher resolution field of view (the small field). Given the known relationship of the resolution fields, the low resolution analysis reveals the presence of an object of interest. The object of interest is moved into the higher resolution field for further detailed analysis while continuing the analysis of the scene or sample at the low resolution to detect any other objects of interest. Thus, a plurality of degrees of resolution analysis can occur substantially simultaneously.

The objects and features of the invention can best be understood from a detailed description of a preferred embodiment thereof, selected for purposes of illustration and shown in the accompanying drawings, in which:

FIG. 2 is a block diagram of the electrical circuitry for analyzing the large field at low resolution, determining if an object of interest is present in the scene, and determining the coordinates thereof;

FIG. 3 is a detailed functional block diagram of the data flow in a representative low resolution analysis;

Figure 1:
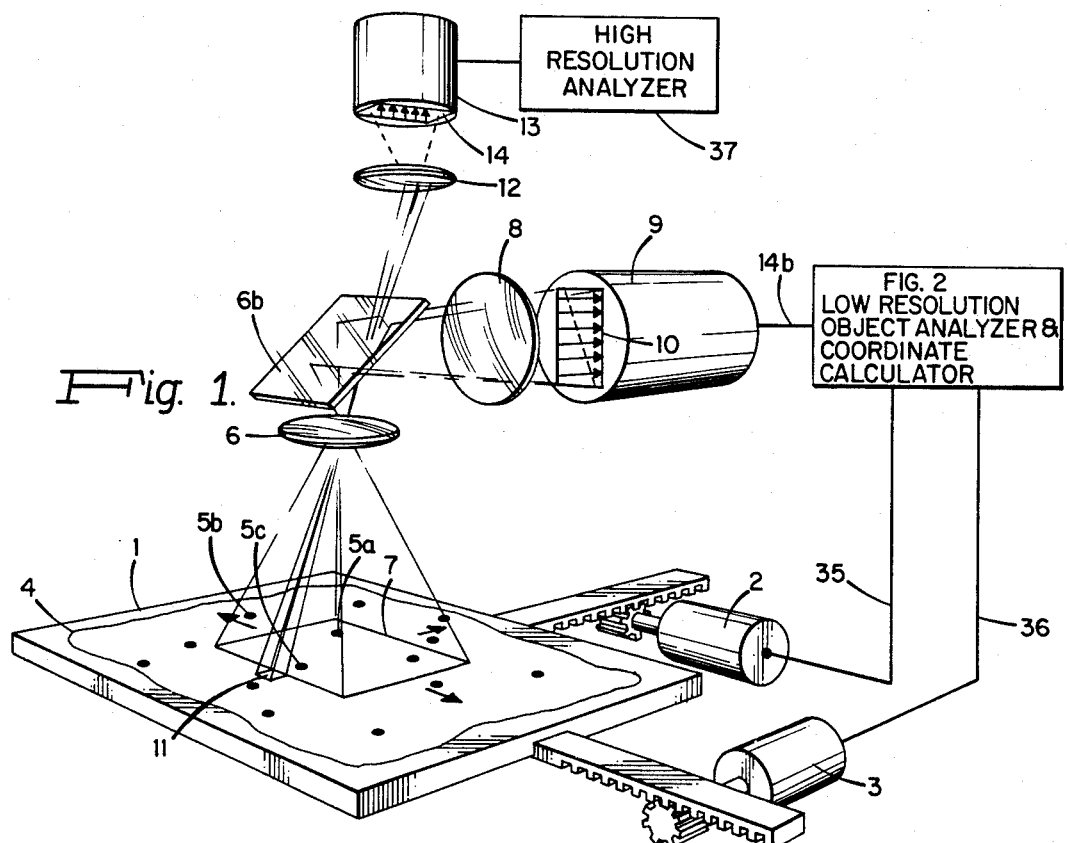
FIG. 1 is a diagrammatic, perspective view of a dual resolution, analysis apparatus constructed in accordance with the present invention.

Turning now to the drawings, FIG. 1 illustrates in diagrammatic form and perspective view, the dual resolution analysis apparatus of the present invention. A sample carrier 1, which can be moved in both the X and Y directions by means of drive motors 2 and 3, contains a sample 4 which has a plurality of objects of interest 5a, 5b, and 5c. In the blood cell embodiment, the sample carrier 1 normally comprises a glass slide upon which the blood sample 4 is spread in a conventional manner. It will be appreciated that the blood sample will contain many red blood cells, a number of dispersed white blood cells of interest i.e. cells 5a, 5b and 5c etc., white cell clumps platelets, platelet clumps, and artifacts such as dust particles and stain precipitate.

A primary optical objective 6, such as a microscope objective, forms an image of an area of the sample. The area of the sample which is designated "a low resolution field" 7 is imaged by the primary objective 6 beam splitter 6b and a low resolution secondary optic 8 onto a low resolution sensor 9. The image of the low resolution field 7 on the low resolution sensor 9 is indicated by the reference numeral 10. A relatively smaller area of the sample, termed a "higher resolution field" 11, is imaged by the primary objective 6 and a secondary high resolution optic 12 onto a high resolution sensor 13. The high resolution image on the high resolution sensor 13 is identified by the reference numeral 14.

Conventional opto-electrical image scanners can be used for the low and high resolution sensors 9 and 11, respectively. For example, the opto-electrical scanning sensors can comprise a television camera, image dissector, photodiode array, or the like. The opto-electrical sensors convert the respective images into electrical signals in a well known manner.

In the preferred embodiment, the low resolution signal output from sensor 9 appears on line 14b and is used to analyze the low resolution field and determine if an object of interest is present, and if so to establish the position of said object of interest (white cell) such as 5a, 5b or 5c relative to the higher resolution field 11, so that appropriate signals can be generated to move the object of interest into the higher resolution field for more detailed analysis. In the embodiment illustrated in FIG. 1, the object of interest is moved into the higher resolution field 11 by moving the sample carrier 1 in the X and Y directions by means of drive motors 2 and 3. It will be appreciated that the equivalent relative movement can be achieved by moving the optical system and leaving the sample carrier fixed. Such an arrangement is illustrated in FIG. 4 and will be discussed subsequently.

Representative circuitry for analyzing the large field at low resolution for a new object of interest, calculating its coordinates and producing appropriate output signals for actuating the drive motors 2 and 3 to move the object of interest into the higher resolution field 11 is depicted in block diagram form in FIG. 2. The low resolution sensor signal output on line 15 is inputed into a low resolution analyzer 16. A number of different analyzers can be used for the low resolution analysis depending on the characteristics of the particular sample under analysis. One such analyzer is described in my U.S. Pat. No. 3,851,156. This analyzer would be employed if an extensive low resolution analysis were desired.

If a simple low resolution analysis were desired, an analyzer can be used which discriminates against objects smaller and/or larger than a predetermined size or shorter and/or longer than a predetermined cord length. This can be accomplished by a particle analysis system such as the $\pi$ MC image analysis system available from Bosch & Lomb Corp., or the Quantimet image analysis system available from Imanco Corp. It is not important to the spirit of the invention whether a relatively complex or relatively simple low resolution image analyzer is employed. The low resolution image analyzer is selected for the particular application at hand.

The low resolution image analyzer 16 outputs a load signal on line 17 when it recognizes an object which warrants further detailed analysis. Assuming that the low resolution scanner 9 scans in a raster fashion and has 64 × 64 resolution elements (resels), the position of the scanner can be tracked by means of 6 bit X and Y counters 19 and 20 respectively. The X and Y counters are reset by means of reset line 21 before the beginning of each scan. During the scan, clock line 18 increments the X counter 19 each time the scanner senses one resel on a horizontal scan line. At the end of each horizontal scan line, the X counter overflows and the overflow signal, on overflow line 22, is used to increment the Y counter 20.

Associated with the X and with Y counters 19 and 20 are corresponding X and Y registers 23 and 24, respectively. The X register 23 is connected to the X counter and the Y register 24 is connected to the Y counter so that when the "load" signal is present on line 17 the contents of the X counter are transferred to the X register and the contents of the Y counter are transferred to the Y register. Thus, when an object of interest is analyzed by the low resolution analyzer 16, the position of that particular object in the low resolution field 7 is stored in the X and Y registers 23 and 24.

The outputs of the X and Y registers appear on output busses 25 and 26. The two output busses feed into corresponding add/subtractors 27 and 28 in which the position of the higher resolution field 11 relative to the low resolution field 7 is subtracted (or added as the case may be) to produce the proper X-move and Y-move signals on output lines 29 and 30. The X and Y motor drive circuitry 31 and 32 transforms the X and Y move signals into electrical signals appropriate to produce the movements represented by the X-move and the Y-move signals.

It should be noted that the FIG. 2 circuitry will have stored the position of the last object in the low resolution field 7 at the end of a scan. However, it will be appreciated that it is possible to inhibit the "load" signals after the first encountered object of interest so that the position of the first object is saved instead of the last object. The X-overflow from Y counter 20 is used to inhibit the command of the motor movements through an "end of scan move enable" circuit 34 until the final change in the X and Y registers 23 and 24.

If a more complex low resolution analyzer, such as that described in my previously mentioned U.S. Pat. No. 3,851,156 and shown in the functional block diagram of FIG. 3, is employed in the present invention, the X and Y position signals are derived from the stored partial features of the cells. This is illustrated in FIG. 3 by the X and Y position outputs. The position information is obtained from the low resolution sensor and is delayed or not delayed in the same manner as the cell data. The Y-overflow signal is replaced by an end of analysis signal to trigger the move enable.

The preceding brief discussion of an illustrated relatively complex low resolution analyzer is directed to the data processing of a single object of interest. It will be appreciated that multiple objects of interest can be handled with suitable storage and processing capability.

It will be appreciated that when the object of interest detected by the low resolution analyzer has been moved into the field of view of the high resolution sensor, the movement also positioned a new scene in the field of view of the low resolution sensor. While the high resolution field is being scanned and analyzed by the high resolution sensor and high resolution analysis means, the low resolution field can be scanned and analyzed by the low resolution sensor and low resolution analyzer to determine if there is another object of interest in the new low resolution field. Thus, when the detailed scan of the object in the high resolution field is complete, the X and Y registers 23 and 24 will contain the coordinates of a new object of interest if one was present in the low resolution field. This feature of the invention which allows the simultaneous or nearly simultaneous analysis of the sample at multiple resolutions results in considerable increase in system speed over a system which must perform these tasks in a sequential manner.

Figure 4A:
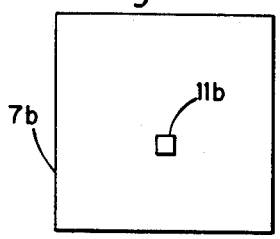
FIGS. 4A through 4D illustrate various relationships between the low resolution field and the higher resolution field and FIG. 5 is another diagrammatic view illustrating an alternative embodiment of the dual resolution analysis apparatus.
Figure 4B:
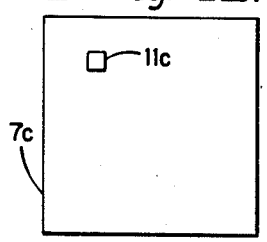
Figures 4C, 4D:
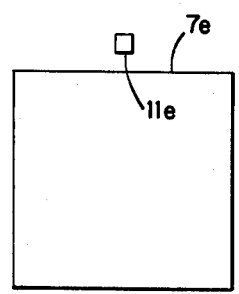

It should also be observed that the relative position of the higher resolution field 11 with respect to the low resolution field 7 as shown in FIG. 1 is only one of a number of possible positions. FIG. 4 illustrates some of the possible relative positions for the two resolution fields. In FIG. 4A, the higher resolution field 11b is shown positioned at the center of the low resolution field 7b. Other locations within the low resolution field can be employed as illustrated in FIG. 4B. The higher resolution field also can partially overlap the low resolution field as illustrated in FIG. 4C or be located entirely outside of the low resolution field as depicted in FIG. 4D. These four arrangements are not intended to be exhaustive, but should be construed as being merely illustrative of a large number of possible arrangements.

Figure 5:
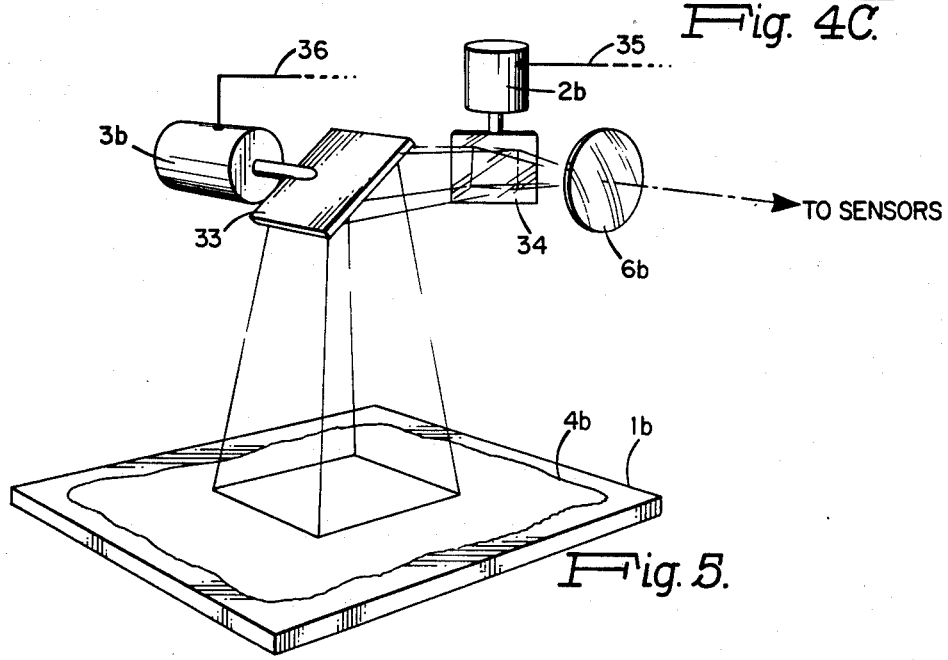

It has been mentioned previously that it is not necessary to physically move the sample carrier 1 in order to move an object of interest into the higher resolution field. Looking at FIG. 5, the sample carrier is identified as 1b and the sample as 4b. Drive motors 2b and 3b are employed to drive movable mirrors 33 and 34 which change the area of the sample 4b scanned by the high and low resolution fields without physically moving the sample. Generally, this particular configuration is practical only if the working distance of the primary optical objective 6b is sufficient to allow the mirrors to be conveniently positioned between it and the sample while maintaining relatively uniform focus.

It will be appreciated that the relative movement of higher resolution field with respect to the object of interest can be accomplished either with or without a corresponding relative movement of the low resolution field 7. In the preferred embodiment, both the low and high resolution fields are moved relative to the object of interest to bring the object of interest into the higher resolution field. However, in the preferred embodiment there is no relative movement between the two resolution fields during the relative movement of the object of interest into the higher resolution field.

The output from the higher resolution sensor 13 is applied to a suitable object analyzer 37. One such analyzer is described in U.S. Pat. No. 3,851,156, for ANALYSIS METHOD AND APPARATUS UTILIZING COLOR ALGEBRA AND IMAGE PROCESSING TECHNIQUES.

Having described in detail a preferred embodiment of my invention, it will now be apparent to those skilled in the art that numerous modifications can be made therein without departing from the scope of the invention as defined in the appended claims.

What I claim and desire to secure by Letters Patent of the United States is:

1. A method for dual resolution analysis of a scene comprising the steps of:
   searching the scene at a low resolution to detect an object therein;
   analyzing the detected object to determine if it is an object of interest; and,
   analyzing the object of interest at a higher resolution while continuing to search the scene at the lower resolution to detect any other objects therein.

2. A method for dual resolution scanning of a sample comprising the steps of:
   scanning a low resolution field of the sample until an object is detected;
   analyzing the detected object to determine if it is an object of interest; and thereafter,
   scanning a higher resolution field containing the object of interest while continuing scanning of the low resolution field to detect any other objects in the sample, said continuing low resolution scanning being performed without moving the sample relative to at least one of said resolution fields.

3. The method of claim 2 further comprising the step of moving the higher resolution field relative to the sample to bring each detected object into the higher resolution field.

4. The method of claim 3 further comprising the step of moving both the low and higher resolution fields relative to the sample while maintaining the same relative position with respect to each other.

5. A dual resolution scene analysis apparatus comprising:
   means for detecting when an object is encounted during the low resolution search;
   means for analyzing the detected object to determine if it is an object of interest;
   means for analyzing the object of interest at a higher resolution;

means responsive to said detected object analyzing means for initiating the object of interest analysis by said higher resolution analyzing means while said low resolution searching means continues to search the scene to detect any other objects therein.

6. A dual resolution scanning apparatus comprising:
means for positioning a sample;
means for scanning a positioned sample at a low resolution, said low resolution scanning means having a low resolution field of view;
means for detecting when a sample object is encountered during the low resolution scan;
means for analyzing the detected sample object to determine if it is an object of interest;
means for scanning the object of interest at a higher resolution, said high resolution scanning means having a high resolution field of view;
means responsive to said object detection means for initiating the object scanning by said high resolution scanning means while said low resolution scanning means continues to scan the sample to detect any other objects in the sample without moving the sample relative to at least one of said resolution fields of view.

7. The apparatus of claim 6 wherein said at least one resolution field is the low resolution field.

8. The apparatus of claim 6 wherein said at least one resolution field is the higher resolution field.

9. The apparatus of claim 6 wherein said low resolution scanning means continues to scan the sample without moving the sample relative to the low and high resolution fields.

10. A dual resolution sample scanning apparatus comprising:
means for positioning a sample;
a first opto-electrical image scanning means for producing an output signal when a sample object is encountered during scanning;
a second opto-electrical image scanning means for producing output signals representative of a scanned image;
optical means for imaging a low resolution sample field on said first opto-electrical image scanning means and a higher resolution sample field on said second opto-electrical image scanning means;
means for analyzing said output signal to determine if an encountered sample object is an object of interest and, if so, producing an object of interest output signal;
means responsive to the object of interest output signal for moving the higher resolution sample field relative to the sample to the sample to bring the encountered sample object into the higher resolution field for scanning by said second opto-electrical image scanning means while the first opto-electrical image scanning means continues to scan the low resolution field to detect any other objects in the sample, said continuing low resolution field scan being performed without moving the sample relative to at least one of said resolution fields; and,
utilization means responsive to the output signals from said second opto-electrical image scanning means.

11. The apparatus of claim 10 where said optical means for imaging said low and higher resolution sample fields has an optical path for the low resolution sample field and an optical path for the higher resolution sample fields.

12. The apparatus of claim 11 wherein said optical paths have a common portion.

13. The apparatus of claim 10 wherein said sample positioning means includes and X-Y movable sample support means and said output signal responsive moving means includes X and Y drive means for moving said sample support means.

14. The apparatus of claim 10 wherein said output signal responsive moving means moves both the low and higher resolution sample fields relative to the sample.

15. The apparatus of claim 14 wherein said moving means moves both the low and higher resolution sample fields relative to the sample without altering the relative relationship of the two fields with respect to each other.

16. The apparatus of claim 15 wherein the higher resolution sample field is positioned within the low sample resolution field.

17. The apparatus of claim 15 wherein the higher sample resolution field and the low sample resolution field partially overlap.

18. The apparatus of claim 15 wherein the higher resolution sample field is positioned outside of the low resolution sample field.

* * * * *